United States Patent [19]
Frey et al.

[11] Patent Number: 6,107,526
[45] Date of Patent: Aug. 22, 2000

[54] PROCESS FOR PRODUCING ETHYL TERTIARY BUTYL ETHER

[75] Inventors: Stanley J. Frey, Palatine; Scott P. Davis, Mount Prospect; Steven L. Krupa, Fox River Grove; Paul R. Cottrell, Arlington Heights, all of Ill.

[73] Assignee: UOP LLC, Des Plaines, Ill.

[21] Appl. No.: 09/099,163

[22] Filed: Jun. 18, 1998

Related U.S. Application Data

[60] Provisional application No. 60/053,383, Jul. 22, 1997.

[51] Int. Cl.$^7$ .................................................. C07C 41/06
[52] U.S. Cl. ........................................... 568/697; 568/699
[58] Field of Search ...................... 568/697, 699

[56] References Cited

U.S. PATENT DOCUMENTS

| | | | |
|---|---|---|---|
| 4,198,530 | 4/1980 | Wentzheimer et al. | 568/697 |
| 4,413,150 | 11/1983 | Briggs | 568/697 |
| 5,158,652 | 10/1992 | Pucci et al. | 203/73 |
| 5,248,836 | 9/1993 | Bakshi et al. | 568/697 |
| 5,258,560 | 11/1993 | Marker | 568/697 |
| 5,368,691 | 11/1994 | Asselineau et al. | 203/29 |
| 5,401,887 | 3/1995 | Rastelli et al. | 568/697 |

*Primary Examiner*—Elli Peselev
*Attorney, Agent, or Firm*—John G. Tolomei; Frank S. Molinaro; Maryann Maas

[57] ABSTRACT

A catalytic distillation process for producing high purity ethyl tertiary butyl ether that contains less than 0.6 weight percent ethanol, and preferably less than 0.07 weight percent ethanol, has been developed. The high purity ethyl tertiary butyl ether is withdrawn directly from a catalytic distillation column; no downstream processing is necessary to remove excess ethanol from the ether product. A stream containing largely normal butane is generated by a $C_4$ distillation column along with a stream containing isobutane. The stream containing isobutane is dehydrogenated to form a stream containing isobutylene. Ethanol, the stream containing isobutylene, and the stream containing largely normal butane are introduced to an etherification zone containing a catalytic distillation column. The catalytic distillation column is operated under conditions which result in the reaction of the ethanol with the isobutylene to form ethyl tertiary butyl ether. Excess ethanol forms an azeotrope with the normal butane and is distilled with other hydrocarbons into an overhead stream. The ethyl tertiary butyl ether and no more than 0.6 weight percent ethanol are distilled into a bottoms stream and withdrawn directly from the catalytic distillation column.

10 Claims, 1 Drawing Sheet

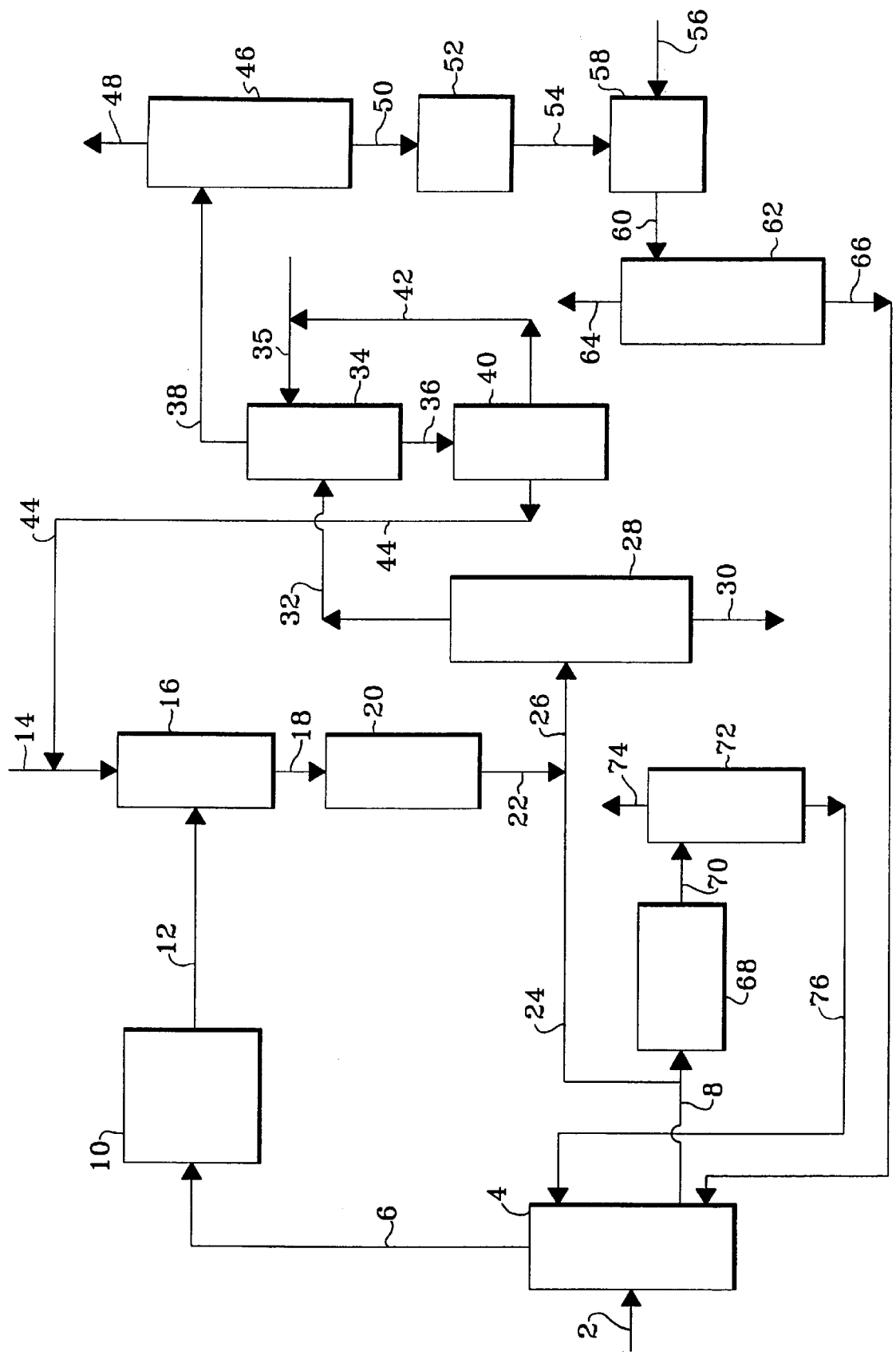

PROCESS FOR PRODUCING ETHYL TERTIARY BUTYL ETHER

This application claims priority of Provisional Application Ser. No. 60/053,383 filed Jul. 22, 1997.

BACKGROUND OF THE INVENTION

Ethers have become an important gasoline blending component in order to increase the octane rating of the gasoline without exceeding regulatory Reid vapor pressure limits and to reduce carbon monoxide emissions. Processes involving catalytic distillation have been used to produce ethers by the reaction of an alcohol with an isoalkene, see U.S. Pat. No. 5,258,560; in particular, catalytic distillation has been used to produce ethyl tertiary butyl ether by the reaction of ethanol and isobutylene. For example, U.S. Pat. No. 5,248,836 discloses passing an isobutylene-containing stream and a stream containing ethanol and ethyl tertiary butyl ether through a straight pass reactor to selectively react ethanol and a portion of the isobutylene to form a first product stream that is sent to a catalytic distillation column. In the catalytic distillation zone the ethyl tertiary butyl ether is largely distilled from the ethanol and isobutylene that are then further reacted to form a second product stream. The distilled ethyl tertiary butyl ether is collected and the second product stream is recycled to the straight pass reactor. U.S. Pat. No. 5,368,691 discloses a configuration for catalytic distillation whereby reaction zones are alternated with, and clearly separated from, distillation zones without a continuous liquid mass between a reaction zone and an adjacent distillation zone.

However, because excess ethanol is usually used to drive the etherification of isobutylene to high conversion and the unreacted ethanol distills with the product ethyl tertiary butyl ether, it is difficult to obtain an ethyl tertiary butyl ether catalytic distillation product having low levels of ethanol. Removing the ethanol from the ethyl tertiary butyl ether product results in a product having a lower Reid vapor pressure, and therefore more valuable. U.S. Pat. No. 5,158,652 discloses a process for separating ethyl tertiary butyl ether and ethanol using two distillation columns operating at different temperatures and pressures. U.S. Pat. No. 5,401,887 discloses a process where the reactants undergo etherification in a reactor and the reactor effluent is sent to a distillation column for separation. The distillation column bottoms containing both ethanol and ethyl tertiary butyl ether is further processed to separate the ethanol from the ethyl tertiary butyl ether by adsorbing the ethanol on a selective adsorbent. U.S. Pat. No. 4,198,530 discloses a process for producing methanol-free methyl tertiary butyl ether. The methyl tertiary butyl ether is formed in an etherification reactor using a feed that contains methanol, $C_4$ hydrocarbons, and a significant amount of normal butene. The reactor effluent is passed to a distillation zone where substantially all of the methanol in the effluent is azeotropically removed together with the $C_4$ hydrocarbons and whereby substantially all of the methanol is removed from the methyl tertiary butyl ether. U.S. Pat. No. 4,413,150 discloses converting isobutylene and an alcohol to an ether and then separating the product ether from the reaction mixture in a single distillation column where the product ether is substantially free of $C_4$ hydrocarbons and alcohol.

Applicants, however, are the first to realize that by routing a stream of largely normal butane from a $C_4$ distillation column to an etherification zone at a point prior to the catalytic distillation column, excess ethanol will be drawn into an azeotrope with the normal butane within the catalytic distillation column and will not be able to contaminate the ethyl tertiary butyl ether product. The result is a high purity ethyl tertiary butyl ether product containing no more than 0.6 weight percent ethanol, and preferably 0.07 weight percent ethanol, available directly from the catalytic distillation column. No further downstream processing is needed for removal of ethanol and purification of the ethyl tertiary butyl ether.

SUMMARY OF THE INVENTION

The purpose of the invention is to provide a catalytic distillation process for producing high purity ethyl tertiary butyl ether that contains less than 0.6 weight percent ethanol, and preferably 0.07 weight percent ethanol. The high purity ethyl tertiary butyl ether is withdrawn directly from a catalytic distillation column. No downstream processing is necessary to remove excess ethanol from the ether product. A stream containing largely normal butane is generated by a $C_4$ distillation column along with a stream containing isobutane. The stream containing isobutane is dehydrogenated to form a stream containing isobutylene. Ethanol, the stream containing isobutylene, and the stream containing largely normal butane are introduced into an etherification zone containing a catalytic distillation column. The catalytic distillation column is operated under conditions which result in the reaction of the ethanol with the isobutylene to form ethyl tertiary butyl ether. Excess ethanol forms an azeotrope with the normal butane and is distilled with other hydrocarbons into an overhead stream. The ethyl tertiary butyl ether and no more than 0.6 weight percent ethanol are distilled into a bottoms stream and withdrawn directly from the catalytic distillation column.

BRIEF DESCRIPTION OF THE DRAWING

The FIGURE is a schematic representation of a specific embodiment of the present invention. The drawing has been simplified by the deletion of a large number of pieces of apparatus customarily employed in processes of this nature that are not specifically required to illustrate the performance of the invention.

DETAILED DESCRIPTION OF THE INVENTION

The present invention provides a process for producing an ethyl tertiary butyl ether stream that contains no more than 0.6 weight percent ethanol, and preferably no more than 0.07 weight percent ethanol, by introducing a largely normal butane stream from a $C_4$ distillation column along with the ethanol and isobutylene reactants to an etherification zone containing a catalytic distillation column. The process begins by distilling a crude $C_4$ stream in a $C_4$ distillation column operating at temperatures ranging from about 30 to about 75° C. and pressures ranging from about 65 to about 185 psig. Crude $C_4$ streams can be obtained from processes such as fluidized catalytic cracking and gas separation plants and generally contain mainly alkanes and alkenes having four carbon atoms. The crude $C_4$ stream is distilled into at least a normal butane-enriched stream and an isobutane-enriched stream. The isobutane is converted into the isobutylene reactant needed in the etherification zone by light hydrocarbon catalytic dehydrogenation processes such as the preferred Oleflex process. A more complete description of the preferred light hydrocarbon catalytic dehydrogenation process can be found in U.S. Pat. No. 5,087,792 and U.S. Pat. No. 5,321,192 which are incorporated by reference and will not be discussed in detail here. While the Oleflex process is the preferred light hydrocarbon catalytic dehydrogenation process, other known dehydrogenation processes may be successfully employed in the present invention. The effluent of the light hydrocarbon catalytic dehydrogenation operation is a mixed $C_4$ stream that includes isobutylene, normal butane, isobutane, normal butene, trans-butene-2 and cis-butene-2. The isobutylene is usually present in an amount ranging from about 10 to about 70 mole percent of the mixed $C_4$ stream. It is contemplated that some propane and propylene may also be present.

The effluent of the light hydrocarbon catalytic dehydrogenation process containing the isobutylene reactant is introduced along with ethanol to an etherification zone. The etherification zone contains a catalytic distillation column and preferably contains at least one fixed bed reactor connected in series to a catalytic distillation column. A greater than stoichiometric amount of ethanol is introduced to the etherification zone in an effort to increase the conversion of isobutylene. Additionally, a stream containing largely normal butane is introduced to the etherification zone at a point prior to the catalytic distillation column portion of the etherification zone. The normal butane is inert in the etherification reaction, but performs an important function in the catalytic distillation column, as discussed below.

The most preferred etherification zone contains two serially-connected fixed bed reactors followed by one catalytic distillation column. The fixed bed reactors are used to perform a large portion of the etherification reaction and the catalytic distillation column allows for conversion beyond that which is achievable in a static system limited by equilibrium. Fixed bed reactors and catalytic distillation are known techniques for the production of ethers, and catalytic distillation involves one or more distillation zones and one or more reaction zones, all located within the same vessel. The distillation zones typically contain distillation structures such as inert packings or distillation trays. The reaction zones contain catalyst capable of catalyzing the etherification reaction and distillation structure for the distillation of components within the reaction zone. The exact fixed bed and catalytic distillation configurations used are not critical to this invention; any known catalytic distillation configuration for the formation of ethers may be used in the practice of this invention. Similarly, the catalyst used in the fixed bed and catalytic distillation columns may be any catalyst known to catalyze the etherification reaction including divinylbenzene cross-linked polystyrene ion exchange resins in which the active sites are sulfonic acid groups, and inorganic heterogeneous catalysts such as boric acid, bismuth molybdate, and metal salts of phosphomolybdic acids wherein the metal is lead, antimony, tin, iron, cerium, nickel, cobalt, or thorium. Boron phosphate, blue tungsten oxide, and crystalline aluminosilicates of the zeolitic molecular sieve type have also been proposed as heterogeneous catalysts for the reaction of ethanol and isobutylene. The conditions at which the reactors are operated are well known and include pressures ranging from about 150 to about 250 psig in the fixed bed reactors and from about 80 to about 120 psig in the catalytic distillation column and temperatures ranging from about 35 to about 75° C. in the fixed bed reactors and from about 45 to about 75° C. in the catalytic distillation column.

As the isobutylene and ethanol contact the catalyst in the fixed bed reactors, the etherification reaction is catalyzed and ethyl tertiary butyl ether is formed. Due to equilibrium limitations, not all of the isobutylene will be consumed and the effluent of the fixed bed reactors contains isobutylene, ethanol, ethyl tertiary butyl ether, trace byproducts and other unreacted hydrocarbons. To react the remaining isobutylene, the effluent is introduced to the catalytic distillation column along with a stream containing largely normal butane. As stated above, the stream containing largely normal butane is introduced to the etherification zone at a point prior to the catalytic distillation column and preferably after the fixed bed reactors.

In the catalytic distillation column, the isobutylene and ethanol contact the catalyst and further etherification is catalyzed. As ethyl tertiary butyl ether is formed, it is immediately distilled and removed from the reactants, thereby facilitating the continuation of the etherification reaction. The product ether is distilled into a bottoms stream and removed from the catalytic distillation column. Most of the other components are distilled into an overhead stream and removed from the catalytic distillation column. A small amount of a few byproducts may distill into the bottoms stream. However, it is known that of the typical products present, ethanol has the highest pure component boiling point and by distillation alone would distill into the ether-containing bottoms stream. The ethanol present in the ether product stream decreases the purity of the ether product, and in order to take advantage of the low blending Reid vapor pressure of the ethyl tertiary butyl ether product, the ethanol contaminant should be no greater than a few tenths of a percent. It is also contemplated that the blending octane number of the product ethyl tertiary butyl ether will be higher when the ethanol contaminant is kept to a minimum. Removal of the ethanol contaminant by techniques such as water extraction, stripping, or adsorption is difficult and costly, and the better approach is to minimize the amount of ethanol contamination occurring in the catalytic distillation column rather than attempt to further process the ether product stream to remove ethanol.

Ordinarily, introducing a significant volume of inert material to a reaction would not be expected to result in increased product purity. Flowing large volumes of inert material through a reaction zone is generally considered to be undesirable as the complete physical structure of the reaction zone must be enlarged to flow the combined volume of reaction mixture and inert material. Correspondingly, the costs of constructing and operating the physically enlarged reaction zone are increased in order to handle the increased total volume. However, in the catalytic distillation column described above, it is extremely beneficial to introduce a large amount of inert normal butane. Specifically, by requiring the independent stream of largely normal butane from the $C_4$ distillation column to be introduced to the catalytic distillation column, virtually all of the excess ethanol is incorporated into an azeotrope with the normal butane and other inert hydrocarbons present and is carried from the catalytic distillation column in the overhead stream thereby leaving little ethanol to contaminate the bottoms ethyl tertiary butyl ether product stream. The bottoms ethyl tertiary butyl ether product stream is of increased purity and contains less ethanol contaminant.

The addition of normal butane is particularly preferred due to the large amount of ethanol incorporated into an ethanol-normal butane azeotrope. For example, at 85 psig, an ethanol-normal butane azeotrope would contain about 2.5 mass percent ethanol, while an isobutane-ethanol azeotrope would contain only 0.5 mass percent ethanol, and a trans-butene-2-ethanol azeotrope or a cis-butene-2-ethanol azeotrope would be essentially nonexistent. This comparatively large azeotropic capacity for ethanol in combination with the overall large concentration of normal butane introduced to the catalytic distillation column causes the unreacted ethanol to form a normal butane-ethanol azeotrope and therefore be unable to distill into the ethyl tertiary butyl ether bottoms stream. The normal butane-ethanol azeotrope is distilled along with other $C_4$ hydrocarbons into the overhead stream of the catalytic distillation column leaving the ethyl tertiary butyl ether product stream with no more than 0.6 weight percent ethanol. It is preferred that the ethyl tertiary butyl ether product stream contain no more than 0.07 weight percent ethanol. The amount of normal butane to be added depends on the operating pressure, the amount of excess ethanol present, the isobutylene converation, and the desired purity of the ether product. In general, the largely normal butane stream should be added in a weight basis ratio ranging from about 2.5:1 to about 8:1 of normal butane to ethanol measured at the point of introduction to the catalytic distillation column. To achieve the preferred limit of ethanol of no greater than about 0.07 weight percent of the ether product stream, the weight basis ratio of normal butane to ethanol measured at the point of introduction to the catalytic distillation column should range from about 5:1 to about 8:1. The above ratios apply when the reactors, both fixed bed and catalytic distillation, are operating at typical design conversions for isobutylene. Should actual conversions fall outside of design expectations, the ratio of normal butane to ethanol required may lie outside the above described ranges.

The ethyl tertiary butyl ether product stream having no more than 0.6 weight percent ethanol can be collected and used in, for example, gasoline blending without further processing. The overhead stream may be treated to conserve and recycle components. For example, the overhead stream from the catalytic distillation column may be conducted along with a water stream to a water extraction unit where the ethanol is separated from the hydrocarbons by extraction with water. The separated ethanol may be dried and recycled to the fixed bed reactors. The drying may be accomplished by distillation, adsorption or a combination of distillation followed by adsorption. The separated water from the drying operation may be recycled to the water extraction unit. The hydrocarbon stream may be distilled to remove any hydrocarbons containing three or less carbon atoms and then additional oxygenates such as diethyl ether may be removed by adsorption. The stream may then undergo treatment with hydrogen to completely saturate any alkenes present. Unconsumed hydrogen is removed by distillation and the hydrocarbon stream is recycled to the $C_4$ distillation column.

In another specific embodiment of the invention, a small amount of hydrogen and a portion of the stream enriched in normal butane from the $C_4$ distillation column are conducted to a catalytic isomerization reactor to form isobutane. The isobutane is recycled to the $C_4$ distillation column. Catalytic butane isomerization processes are known in the art, and it is not critical which process is chosen for use in the present invention.

Without intending any limitation on the scope of the present invention and as merely illustrative, this invention is explained below in specific terms as applied to a particular embodiment of the invention. Turning now to the figure, a crude $C_4$ stream 2 as described above is introduced to a $C_4$ distillation column 4 operating at a pressure of 110 psig and a temperature of 49° C. A stream containing approximately 98 weight percent isobutane is separated and removed by line 6 and a stream containing approximately 98 weight percent normal butane is separated and removed via line 8. A portion of the line 8 stream is removed by line 24 and routed downstream as discussed below.

The stream enriched in isobutane is conducted through line 6 to light hydrocarbon catalytic dehydrogenation reactor 10 which contains a catalyst having a platinum component, a Group IVA component, and an alkali or alkaline earth component, a halogen component and a porous carrier material and is operated at a pressure of 25 psig and a temperature of 645° C. The effluent from reactor 10 contains approximately 40 weight percent isobutylene, 53 weight percent isobutane, less than 2 weight percent each of butene-1, trans-butene-2, and cis-butene-2, and 4 weight percent of hydrocarbons having three carbon atoms. Hydrogen generated in reactor 10 is also removed (not shown). The effluent from reactor 10 is conducted via line 12 to a first fixed bed etherification reactor 16. Ethanol is also conducted to reactor 16 via line 14. The amount of ethanol in line 14 is about 1.01:1 ethanol to isobutylene. Reactor 16 contains a resin catalyst and is operated at a pressure of 225 psig and a temperature of 40° C. In reactor 16, a portion of the isobutylene is converted to ethyl tertiary butyl ether.

Reactor 16 additionally incorporates an effluent recycle stream to aid in cooling the reactor and controlling the temperature of operation (not shown). The remainder of the effluent of reactor 16 that is not recycled is conducted via line 18 to a second fixed bed etherification reactor 20 having the same catalyst and operating at the same conditions as reactor 16. The etherification reaction continues in reactor 20 and produces an effluent which is removed via line 22 and contains approximately 54 weight percent ethyl tertiary butyl ether, 37 weight percent isobutane and less than 2 weight percent each of isobutylene, normal butane, butene-1, trans-butene-2 and cis-butene-2 and 4 weight percent of hydrocarbons having three carbon atoms.

Line 22 is now combined with the line 24 to provide line 26 which is introduced to catalytic distillation column 28. Catalytic distillation column 28 contains a resin catalyst and is operated at a pressure of 89 psig and a temperature of 52° C. at the top of the unit. As the mixture in line 26 contacts the catalyst, additional etherification is catalyzed. The product ether is immediately distilled from the reactants thereby allowing the etherification reaction to continue. Excess ethanol forms an azeotrope mainly with the normal butane and partially with the other $C_4$ hydrocarbons present and is distilled with the hydrocarbons into a catalytic distillation column overhead stream which is removed via line 32. The general composition of catalytic distillation column overhead stream is about 1.4 weight percent ethanol, 28 weight percent normal butane, 64 weight percent isobutene, 4 weight percent of hydrocarbons having 3 carbon atoms and less than 2 weight percent each of isobutylene, butene-1, trans-butene-2, cis-butene-2 and other byproducts. With the excess ethanol incorporated into an azeotrope with normal butane, the product ethyl tertiary butyl ether bottoms stream removed from catalytic distillation column 28 via line 30 contains no more than 0.07 weight percent ethanol.

To recover and recycle usable components, the catalytic distillation column overhead stream removed via line 32 is further processed as follows. Water via line 35 and the catalytic distillation column overhead stream via line 32 are conducted to a water extraction unit 34 in order to separate ethanol from the hydrocarbons by extraction with water. A water and ethanol stream is removed via line 36 and a hydrocarbon stream is removed via line 38. Line 36 is conducted to a distillation column 40 where the water and ethanol are separated by distillation. Optionally, an adsorption unit may also be used to further separate the water and ethanol (not shown). The complete removal of water from the ethanol reduces the formation of byproducts, such as tertiary butyl alcohol, upon recycle. A water-enriched stream conducted via line 42 is removed from distillation column 40 and recycled to combine with water line 35 and an ethanol-enriched stream is removed via line 44 from drier 40 and recycled to combine with ethanol stream 14. The hydrocarbon stream conducted via line 38 is introduced to distillation column 46 where hydrocarbons containing three or fewer carbon atoms are separated by distillation at 210 psig and 43° C. and removed via line 48. The remaining hydrocarbons, 15 weight percent normal butane, 82 weight percent isobutane, less than 2 weight percent each of isobutylene, butene-1, trans-butene-2, cis-butene-2 and byproducts are conducted via line 50 to an oxygenate removal unit 52 which contains an adsorbent capable of selectively adsorbing byproduct oxygenates. An oxygenate-depleted hydrocarbon stream is removed via line 54 and conducted to hydrogenation unit 58 which contains a palladium hydrogenation catalyst and is operated at 300–400 psig and a temperature from about 40 to about 50° C. Hydrogen is introduced via line 56 to hydrogenation unit 58 and unsaturated compounds which may be present are hydrogenated. A saturated hydrocarbon stream is removed from hydrogenation unit 58 via line 60 and is conducted to distillation column 62 operated at 305 psig and 107° C. Excess hydrogen is removed via line 64 and a hydrocarbon stream containing 20 weight percent normal butane and 80 weight percent isobutane is conducted from distillation column 62 via line 66 and recycled to distillation column 4.

To make more efficient use of the excess normal butane in the crude $C_4$ hydrocarbon mixture of line 2, a portion of the stream enriched in normal butane is conducted via line 8 to isomerization reactor 68. Isomerization reactor 68 contains a fixed bed of isomerization catalyst containing platinum plus a halogen component and is operated at a pressure of 450 psig and a temperature of about 150 to about 200° C. As the normal butane contacts the catalyst, a portion of the normal butane is isomerized to form isobutane. The effluent of isomerization reactor 68 contains a mixture of normal butane and isobutane and is conducted via line 70 to distillation column 72. Distillation column 72 is operated at a pressure of from about 280 psig to about 330 psig and a temperature of about 38° C. and distills hydrocarbons having three or fewer carbon atoms into an overhead stream which are removed by line 74. A mixture of normal butane and isobutane is distilled into a bottoms stream and is removed and recycled via line 76 to the $C_4$ distillation column 4.

It must be emphasized that the above description is merely illustrative of a preferred embodiment and is not intended as an undue limitation on the generally broad scope of the invention. Moreover, while the description is narrow in scope, one skilled in the art would understand how to extrapolate to the broader scope of the invention. For example, the operation at different conditions or using different downstream processing depending upon the application can be readily extrapolated from the foregoing description.

What is claimed is:

1. A process for producing an ethyl tertiary butyl ether stream containing less than 0.6 weight percent ethanol comprising:
    a) separating, in a $C_4$ distillation column, a mixed $C_4$ hydrocarbon stream into at least a stream enriched in normal butane and a stream enriched in isobutane;
    b) catalytically dehydrogenating the stream enriched in isobutane to form an effluent containing isobutylene;
    c) introducing ethanol, the effluent containing isobutylene, and the stream enriched in normal butane to an etherification zone having a catalytic distillation column which contains an etherification catalyst, said stream enriched in normal butane being introduced in an amount sufficient to form an azeotrope with unreacted ethanol and thereby provide an ethyl tertiary butyl ether product stream containing no more than 0.6 weight percent ethanol and an overhead stream containing an azeotrope of ethanol and normal butane;
    d) removing the ethyl tertiary butyl ether product stream containing less than about 0.6 weight percent ethanol from the catalytic distillation column; and
    e) removing the overhead stream from the catalytic distillation column.

2. The process of claim 1 wherein the stream enriched in normal butane is introduced to the catalytic distillation column in an amount sufficient to provide a weight ratio in the range of from about 2.5:1 to about 8:1 of normal butane to ethanol measured at the inlet to the catalytic distillation column.

3. The process of claim 1 wherein the ethyl tertiary butyl ether stream contains less than 0.07 weight percent ethanol and the effluent containing isobutylene and the stream enriched in normal butane are introduced to the etherification zone containing a catalytic distillation column in amounts sufficient to provide a weight ratio in the range of from about 5:1 to about 8:1 of normal butane to ethanol measured at the inlet to the catalytic distillation column.

4. The process of claim 1 wherein the effluent containing isobutylene contains from about 10 to about 70 mole percent isobutylene.

5. The process of claim 1 wherein the etherification zone contains at least one fixed bed reactor serially connected to at least one catalytic distillation column.

6. The process of claim 5 wherein the stream enriched in normal butane is introduced to the etherification zone at a point after the fixed bed reactor and before the catalytic distillation column.

7. The process of claim 1 further comprising:
    a) extracting with water, in a water extraction unit, overhead stream containing an azeotrope of ethanol and normal butane of 1(c) to form an ethanol-depleted stream enriched in normal butane and a stream enriched in water and ethanol;
    b) separating the stream enriched in water and ethanol to form a stream enriched in ethanol and a stream enriched in water;
    c) recycling the stream enriched in ethanol to the etherification zone of 1(c); and
    d) recycling the stream enriched in water of 7(b) to the water extraction unit of 7(a).

8. The process of claim 7 further comprising recycling the ethanol-depleted stream enriched in normal butane of 7(a) to the etherification zone of 1(c).

9. The process of claim 1 further comprising:
    a) water extracting, in a water extraction unit, the overhead stream containing an azeotrope of ethanol and normal butane of 1(c) to form an ethanol-depleted stream enriched in normal butane and a stream enriched in water and ethanol;
    b) removing hydrocarbons having three or less carbon atoms from the ethanol-depleted stream enriched in normal butane by distillation to form a stream depleted of hydrocarbons having three or less carbon atoms;
    c) removing oxygenates from the stream depleted of hydrocarbons having three or less carbon atoms by adsorption to form an oxygenate-depleted stream;

d) saturating alkenes in the oxygenate-depleted stream by hydrogenation to form an alkene-depleted stream;

e) separating, by distillation, the alkene-depleted stream into a stream enriched in hydrogen and a stream enriched in alkanes having four carbon atoms;

f) recycling the stream enriched in alkanes having four carbon atoms to the $C_4$ distillation column of 1(a); and g) removing the stream enriched in hydrogen.

10. The process of claim 1 further comprising:

a) catalytically isomerizing a portion of the stream enriched in normal butane of 1(a) to form a second stream enriched in isobutane; and b) recycling the second stream enriched in isobutane to the $C_4$ distillation column of 1(a).

* * * * *